United States Patent [19]

Bonte et al.

[11] Patent Number: 5,723,149
[45] Date of Patent: Mar. 3, 1998

[54] USE OF MEDICAGO SAPONINS FOR THE PREPARATION OF COSMETIC OR PHARMACEUTICAL COMPOSITIONS, ESPECIALLY DERMATOLOGICAL COMPOSITIONS, PROMOTING RENEWAL OF THE EPIDERMIS, STIMULATING HAIR REGROWTH OR DELAYING HAIR LOSS

[75] Inventors: Frédéric Bonte; Alain Meybeck, both of Courbevoie; Georges Massiot, Reims, all of France

[73] Assignee: LVMH Recherche, Colombes, Cedex, France

[21] Appl. No.: 596,699

[22] Filed: Feb. 5, 1996

Related U.S. Application Data

[63] Continuation of Ser. No. 326,048, Oct. 19, 1994, abandoned, which is a continuation of Ser. No. 64,126, filed as PCT/FR91/00818, Oct. 18, 1991, published as WO92/09262, Jun. 11, 1992, abandoned.

[30] Foreign Application Priority Data

Nov. 21, 1990 [FR] France ................... 90 14542

[51] Int. Cl.$^6$ ............... A61K 9/127; A61K 31/70
[52] U.S. Cl. .............. 424/450; 424/195.1; 424/70.1; 424/401; 514/23; 514/33; 514/34; 514/880; 514/881
[58] Field of Search ................ 424/450, 401, 424/70.1, 195.1; 514/844–848, 880, 881, 23, 33, 34

[56] References Cited

U.S. PATENT DOCUMENTS

| | | | |
|---|---|---|---|
| 4,318,906 | 3/1982 | Llopart | 424/195 |
| 4,339,442 | 7/1982 | Takemoto | 424/182 |
| 4,800,080 | 1/1989 | Grollier | 426/74 |
| 4,879,376 | 11/1989 | Foresta | 536/18.1 |
| 4,880,630 | 11/1989 | Novak | 424/195.1 |
| 4,994,378 | 2/1991 | Berger | 435/29 |
| 5,165,935 | 11/1992 | Andre | 426/450 |
| 5,166,139 | 11/1992 | Bombardelli | 514/26 |
| 5,166,176 | 11/1992 | Obagi | 514/557 |
| 5,182,373 | 1/1993 | Kim | 536/4.1 |
| 5,238,965 | 8/1993 | Piazza | 514/844 |

FOREIGN PATENT DOCUMENTS 2187328  1/1974  France.

OTHER PUBLICATIONS

*Chemical Abstracts*, vol. 90, No. 12, Mar. 19, 1979 (Columbus, Ohio, US) see page 304, abstract 92411u, and US. A. 865985 (Malinow, M.R.) Jul. 7, 1978.

*Chemical Abstracts*, vol. 75, No. 8, Aug. 23, 1971 (Columbus, Ohio, US), B. Gestetner, et al.: "Lucerne saponins. IV. Relation between their chemical constitution, and hemolytic, and antifungal activities," see page 237, abstract 52715e, and J. Sci. Food Agr. 1971, 22(4), 168–72.

Mezei Life Sciences 26, 1473, 1980.

*Primary Examiner*—Gollamudi S. Kishore
*Attorney, Agent, or Firm*—Beveridge, DeGrandi, Weilacher & Young, L.L.P.

[57] ABSTRACT

The invention relates to the use of Medicago saponins for the preparation of cosmetic or pharmaceutical compositions. The invention provides for the incorporation of 0.01% to 5% by weight of a saponin or a corresponding sapogenin, or a plant extract in which it is present, originating in particular from lucerne leaves or roots. The invention makes it possible to promote renewal of the epidermis, stimulate hair regrowth or delay hair loss, or else to combat the effects of ageing on the state of the skin and scalp, as is evident from the FIGURE.

23 Claims, 1 Drawing Sheet

USE OF MEDICAGO SAPONINS FOR THE PREPARATION OF COSMETIC OR PHARMACEUTICAL COMPOSITIONS, ESPECIALLY DERMATOLOGICAL COMPOSITIONS, PROMOTING RENEWAL OF THE EPIDERMIS, STIMULATING HAIR REGROWTH OR DELAYING HAIR LOSS

This application is a continuation of application Ser. No. 08/326,048, filed Oct. 19, 1994, now abandoned, which application is entirely incorporated herein by reference, which is a continuation of application Ser. No. 08/064,126, filed May 21, 1993, now abandoned, which is a 371 of PCT/FR91/00818 filed on Oct. 18, 1991, which application is entirely incorporated herein by reference.

The present invention relates essentially to the use of Medicago saponins or corresponding sapogenins for the preparation of cosmetic or pharmaceutical compositions, especially dermatological compositions, intended in particular for promoting renewal of the epidermis, stimulating hair regrowth or delaying hair loss, and for combating the effects of ageing on the state of the skin and scalp.

The plants of the genus Medicago, often designated by the generic term "lucernes", are Leguminosae which are widespread on the planet in temperate zones and in certain arid regions, either in the wild state or in the cultivated state as animal fodder.

Medicago sativa or alfalfa, correctly called lucerne, is the principal representative of this family. By plants of the genus Medicago are present on the five continents, especially in France, in the mediterranean basin, in the United States, in Canada and in Australia. The following may be mentioned among the other Medicago species: M. lupulina (Canada), M. truncatula (Australia, South Africa), M. laciniata (arid and semi-arid zones of Australia, Saudi Arabia, Libya), M. littoralis (Australia), M. minima (Algeria), M. falcata (USSR, Canada), M. media (Alaska) and M. arborea (Greece).

The lucernes contain a large variety of substances useful for feeding animals and humans, especially proteins, vitamins, carotenoids and mineral salts (J. G. COORS et al., Crop Science, 1986, vol. 26, no. 5, p. 843–848; E. M. BICKOFF et al. in Alfalfa Science and Technology, ed. C. H. HANSON, published by The American Society of Agronomy, Madison, Wis., USA, 1972, p. 247–282). The leaves and especially the roots also contain glycosylated compounds consisting essentially of triterpene saponins described in particular by G. MASSIOT et al., J. Chem. Soc. Perkin Trans. I (1988) p. 3071–3079. Hydrolysis of the glycosidic linkages of these saponins yields the corresponding triterpene sapogenins, the most abundant of which is medicagenic acid (G. Massiot et al., J. Agric. Food Chem., 1988, vol. 36, p. 902–909). Finally, sterol glycosides, present in very small amounts, have been identified by S. ITO et al., Nippon Nogei Kagaku Kaishi 1973, vol. 47, no. 3, p. 229–230, in particular beta-sitosteryl glucoside and stigmasteryl glucoside.

A number of therapeutic uses of extracts or substances extracted from lucerne—Medicago sativa—have been described.

Thus it has been recommended to administer lucerne sap in order to treat avitaminosis and decalcification (Aldo Poletti, "Fleurs et Plantes médicinales" ("Medicinal Flowers and Plants"), ed. Delachaux and Niestlé, p. 126) and the seed extract has been described in the document SU-624 634 as possessing an antiinflammatory activity. Also, a lucerne extract has been described in the document FR-2 571 256 as possessing an estrogenic activity, its application being in the treatment of cellulitis. The above-mentioned medicagenic acid possesses a hemolytic activity (B. GESTETNER et al., Experientia, 1971, 27(1), 40–41) and an antifungal activity (DE-3 717 280).

Finally, the use in cosmetics of the sterol glucosides present in the leaves has been described in the document JP-62-72 604 as promoting hydration of the skin.

The above-mentioned effects of ageing on the skin are characterized in particular by a slowing-down of the cell differentiation of the epidermis, especially the keratinocytes, leading to a slowing-down of their renewal and their activity, which gives the skin a duller, dry and more wrinkled appearance. Ageing also has adverse effects on the hair follicles. For the keratinocytes of the follicles, as for those of the epidermis, these effects cause a reduction in activity, leading to a slowing-down of hair growth and, ultimately, a degeneration of the follicle and the definitive loss of the hair.

One object of the present invention is to solve the novel technical problem which consists in providing a novel formulation of a cosmetic or pharmaceutical composition, especially a dermatological composition, which is effective in respect of renewal of the epidermis, hair regrowth and the prevention or slowing-down of hair loss, as well as in combating the effects of ageing on the state of the skin and scalp.

A further object of the present invention is to solve this novel technical problem in a particularly simple manner which can be used on the industrial scale.

The present invention makes it possible to solve this technical problem for the first time in a satisfactory manner which can be used on the industrial scale.

Thus, according to a first feature, the present invention relates to the use of at least one Medicago triterpene saponin or at least one corresponding sapogenin, or a plant extract in which it is present, for the manufacture of a cosmetic or pharmaceutical composition, especially a dermatological composition, intended in particular for promoting renewal of the epidermis, stimulating hair regrowth or delaying hair loss, and for combating the effects of ageing on the state of the skin and scalp.

In one particular variant, the above-mentioned saponin and plant extract are obtained by extraction from aerial parts, such as leaves or stems, or roots of Medicago, preferably from roots of this plant. Particularly preferably, the parts of the plant which are used are dried prior to the extraction treatment.

In another variant, the above-mentioned saponin and plant extract are obtained by extraction from calluses obtained by the in vitro culture of tissues of Medicago, in particular from root tissues of this plant, for example by the technique described by BESSON V. et al. in Phytochemistry 1989, vol. 28, no. 5, pages 1379 and 1380.

In one advantageous variant, the above-mentioned saponin is selected from those containing a carboxyl group and is used in the acid form for carrying out the present invention.

In another embodiment, the above-mentioned sapogenin is preferably selected from the group consisting of lucernic acid, medicagenic acid, zanhic acid, bayogenin, hederagenin and soyasapogenols A, B, C and E.

In yet another variant of the invention, the above-mentioned Medicago plant is selected from the group consisting of: Medicago sativa, Medicago lupulina, Medicago truncatula, Medicago laciniata, Medicago littoralis, Medicago falcata, Medicago media, Medicago minima, Medicago varia, Medicago arborea and Medicago romanica.

In yet another particular embodiment of the invention, the above-mentioned plant extract is obtained by the method which is described below by way of indication but without implying any limitation. The dry matter, preferably consisting of Medicago roots, is extracted by means of a solvent selected from the group consisting of: water, alcohols preferably containing from 1 to 4 carbon atoms, and organic esters preferably containing from 3 to 6 carbon atoms, or by means of a mixed solvent based on any mixture of the above-mentioned solvents.

Advantageously, the primary extraction solvent is methanol, ethanol, a methanol/water mixture or an ethanol/water mixture.

The ratio of the plant material to the extraction agent is not critical and will generally be between 1:5 and 1:20 parts by weight.

The above-mentioned primary extraction is effected at temperatures between room temperature and the boiling point of the solvent used for the extraction.

Preferably, the primary extraction is effected under reflux for a period of 2 to 4 h under atmospheric pressure. Also, it is advantageously preceded by cold maceration for 2 to 4 h in the extraction solvent.

When extraction has ended, the solvent phase containing the extract is filtered and then concentrated and/or evaporated to dryness under reduced pressure to give a first, saponin-rich extract according to the invention.

In one particular variant, the use according to the invention relates to a mixture of above-mentioned saponins. A mixture of saponins according to the invention is obtained in particular from the above-mentioned first concentrated or dry extract by the procedure indicated below. The above-mentioned first extract is introduced into and then agitated in an apolar solvent which is preferably miscible with the primary extraction solvent, such as an ether or a ketone of low molecular weight, in particular ethyl or isopropyl ether, acetone or methyl ethyl ketone. The amount by weight of apolar solvent is generally 5 to 100 parts to one part of primary extract. The insoluble material and/or the precipitate formed contains principally a mixture of saponins according to the invention.

Advantageously, the mixture of saponins obtained above is purified by any method accessible to those skilled in the art.

In particular, the above-mentioned insoluble material and/or precipitate is redissolved in about 20 times its weight of water. The aqueous solution is then extracted 3 to 4 times with a sparingly water-soluble alcohol, such as butanol, saturated with water, for example in proportions of 1/1 by volume for each extraction operation. The alcohol phases are combined and evaporated under reduced pressure. The residue is dissolved in about 10 times its weight of water and the solution is then dialyzed against pure water for 4 to 5 days. The contents of the dialysis cell are lyophilized. If it is appropriate to further improve the purification of the mixture of saponins obtained, the lyophilizate is dissolved in methanol and then discharged into ethyl ether. The precipitate formed is collected.

Advantageously, the mixture of saponins obtained is subjected to an additional treatment consisting for example in passing an aqueous solution of said mixture over an acid cation exchange resin and then eluting it with water or a methanol/water mixture, the purpose of said additional treatment being to convert to the acid form those saponins which contain a salified carboxyl group.

The above-mentioned sapogenins according to the invention are preferably obtained from the saponins extracted by the method described above. This is done by hydrolyzing the glycosidic linkages of said saponins. Advantageously, acid hydrolysis is carried out, especially with halogen-containing acids such as perchloric acid, fluoboric acid or trifluoroacetic acid, in the manner described for example in the publication by G. Massiot et al. in Journal of Agricultural and Food Chemistry 1988, vol. 36, p. 902–909.

In another advantageous variant of the invention, the above-mentioned saponin or the above-mentioned corresponding sapogenin, or the above-mentioned lucerne extract, is at least partially incorporated into a hydrated lipidic lamellar phase or into vesicles of the liposome type.

The term "lipidic" in the expression "lipidic lamellar phase" covers all substances comprising a so-called fatty hydrocarbon chain generally containing more than 5 carbon atoms, this substance usually being called a "lipid".

According to the invention, the lipids used to form the lipidic lamellar phase or the vesicles of the liposome type are amphiphilic lipids, i.e. lipids consisting of molecules possessing a hydrophilic group, which can equally well be ionic or non-ionic, and a lipophilic group, these amphiphilic lipids being capable of forming a lipidic lamellar phase or vesicles of the liposome type, in the presence of an aqueous phase, according to the amount of water in the mixture.

The following may be mentioned in particular among these lipids: phospholipids, phosphoaminolipids, glycolipids, polyoxyethyleneated fatty alcohols and optionally polyoxyethyleneated polyol esters. Such substances consist for example of an egg or soya lecithin, a phosphatidylserine, a sphingomyelin, a cerebroside, a glycosyl ceramide or an oxyethyleneated polyglycerol stearate.

It is preferred according to the invention to use a lipid mixture consisting of at least one amphiphilic lipid and at least one hydrophobic lipid such as a sterol like cholesterol or beta-sitosterol. The amount of hydrophobic compounds, expressed by weight, must not generally exceed the amount of amphiphilic lipids and preferably must not exceed 0.5 times this amount.

In one preferred variant, the above-mentioned saponin is introduced into the aqueous phase of the hydrated lipidic lamellar phase or the liposomes at a concentration of between 0.01% and 5% by weight, based on the total weight of said aqueous phase.

In yet another preferred variant, the above-mentioned sapogenin is incorporated into the lipidic phase of the hydrated lipidic lamellar phase or the liposomes at a concentration preferably of between 0.01% and 30% by weight of said lipidic phase. In this case, it is not generally necessary to add another hydrophobic constituent, such as a sterol, to the lipidic phase. The above-mentioned concentration is particularly preferably between 0.01% and 10% by weight of this lipidic phase.

The incorporation of the above-mentioned saponins or sapogenins or the above-mentioned extracts according to the invention into hydrated lipidic lamellar phases or into liposomes can be carried out by the known preparative techniques described for example in the document EP-B1-0 087 993=U.S. Pat. No. 4,508,703, if appropriate in combination with the document EP-B1-0 101 559=U.S. Pat. No. 4,621, 023.

According to a second feature, the present invention further relates to a cosmetic or pharmaceutical composition, especially a dermatological composition, intended in particular for promoting renewal of the epidermis, stimulating hair regrowth or delaying hair loss, and for combating the effects of ageing on the state of the skin and scalp, which composition comprises, as the active ingredient, an effective amount of at least one Medicago triterpene saponin or at least one corresponding sapogenin, or at least one plant extract in which it is present, if appropriate in a cosmetically or pharmaceutically acceptable excipient, carrier or vehicle.

Preferably, the above-mentioned saponin, the above-mentioned sapogenin or the above-mentioned extract is obtained from aerial parts, such as leaves or stems, or roots of Medicago, preferably from roots of this plant.

Diverse variants of the composition are clearly apparent from the above description relating to the use.

In particular, the above-mentioned saponin or sapogenin or the above-mentioned plant extract can advantageously be at least partially incorporated into hydrated lipidic lamellar phases or into vesicles of the liposome type.

Furthermore, in one advantageous variant, the concentration of above-mentioned saponin or sapogenin or above-mentioned plant extract is preferably between 0.001% and 5% and particularly preferably between 0.01 and 2% by weight, based on the total weight of the cosmetic or pharmaceutical composition.

These proportions are understood as being by dry weight where plant extracts are concerned.

In another advantageous variant of the invention, the cosmetic or pharmaceutical composition, especially the dermatological composition, according to the invention also comprises an effective concentration of at least one other active substance selected from xanthines, vitamins, in particular vitamins A, B and E, tyrosine or its derivatives, for example glucose tyrosinate and malyltyrosine, quinine or its derivatives, rubefacients such as methyl nicotinate, a papilla fibroblast culture supernatant such as that described in the document EP-A-272 920, keratin hydrolyzates, trace elements such as zinc, selenium and copper, 5-α-reductase inhibitors such as: progesterone, cyproterone acetate and Minoxidil®, azelaic acid and its derivatives, a 1,4-methyl-4-azasteroid, in particular 17-β-N,N-diethylcarbamoyl-4-methyl-4-aza-5-α-androstan-3-one, or else an extract of Serenoa repens. Advantageously, this active substance can be at least partially incorporated into hydrated lipidic lamellar phases or into vesicles of the liposome type.

The cosmetic or pharmaceutical compositions, especially the dermatological compositions, according to the present invention can be applied topically, in particular for promoting renewal of the epidermis, stimulating hair regrowth or delaying hair loss, and for combating the effects of ageing on the state of the skin and scalp, in particular in compositions presented in the form of creams, gels or lotions for topical application.

Within this feature, the present invention further provides a method of treating the epidermis, intended especially for promoting its renewal, or a method of treating the hair, intended for promoting its regrowth or delaying its loss, which method comprises the topical application, in an amount effective for achieving said desired effect, of at least one Medicago saponin or at least one corresponding sapogenin, or a plant extract in which it is present. In one advantageous variant, said above-mentioned saponin or sapogenin or said plant extract is at least partially incorporated into a hydrated lipidic lamellar phase or into vesicles of the liposome type.

It should be noted that, in the present description and in the claims, the expression "at least partially into hydrated lipidic lamellar phases or into vesicles of the liposome type" is understood as meaning that the above-mentioned active ingredient is combined with hydrated lipidic lamellar phases or with vesicles of the liposome type, whatever form this combination may take.

However, it is clear that such a combination can constitute incorporation or even encapsulation in the hydrated lipidic lamellar phases or in the vesicles of the liposome type, although it is not necessary for all this active ingredient to be incorporated or encapsulated in order to obtain the desired effect, especially on the epidermis and on the scalp.

According to another feature, the invention further provides a method of manufacturing a cosmetic or pharmaceutical composition, especially a dermatological composition, intended in particular for promoting renewal of the epidermis, stimulating hair regrowth or delaying hair loss, and for combating the effects of ageing on the state of the skin and scalp, which method comprises using at least one Medicago saponin or at least one corresponding sapogenin, or a plant extract in which it is present, and mixing it with a pharmaceutically or cosmetically acceptable excipient, vehicle or carrier. In one variant, this method comprises firstly at least partially incorporating at least one above-mentioned saponin or at least one corresponding sapogenin, or a plant extract in which it is present, into hydrated lipidic lamellar phases or into vesicles of the liposome type and then mixing them with a pharmaceutically or cosmetically acceptable excipient, vehicle or carrier.

Other objects, characteristics and advantages of the invention will become clearly apparent from the following explanatory description referring to several Examples which are given solely by way of illustration and which consequently cannot limit the scope of the invention in any way.

BRIEF DESCRIPTION OF THE DRAWING

The accompanying single FIGURE reports test results on the pilary cycle of Sprague Dawley rats with the percentage of hairs in anagenetic phase comprising the Y-axis as a function of the number of days on the X-axis as reported in detail in Example 13, the curve joining the squares corresponding to the results obtained with the mixture of saponins extracted from lucerne roots, of Example 2, according to the invention, the curve joining the crosses being obtained with the excipient and finally the curve joining the dots being obtained with the control group not receiving any product.

In the Examples, the percentages are expressed by weight, unless indicated otherwise. In the case of extracts, the percentages are expressed by dry weight of the extract.

Example 1

Preparation of a saponin-rich extract of roots of lucerne (Medicago sativa)

200 g of dry and powdered lucerne roots are macerated for 2 h in 1.2 l of methanol. The mixture is refluxed for 3 h. After cooling, the solution is filtered on a no. 3 glass frit. The residues are re-extracted in the same way with 2 times 1 l of methanol. The three filtrates are combined and concentrated on a rotary evaporator to a volume of about 500 ml.

This gives a first, saponin-rich crude extract, which is purified in the following manner.

The concentrated solution is added rapidly to 2.5 l of distilled acetone; the precipitate which forms is collected on a no. 4 glass frit, washed with acetone and drained. The precipitate is placed in a desiccator ($CaCl_2$) and is kept under reduced pressure for several hours by means of a vane pump. Yield=18 g (9%).

In one variant, the methanol in the method described above can be replaced with a 20% methanol/water mixture. However, the yield is slightly lower in this case.

Example 2

Preparation of a mixture of saponins from roots of lucerne (Medicago sativa)

1 kg of powdered lucerne roots is taken and macerated in 6 l of methanol for 2 h. The suspension is refluxed for 3 h. After cooling, it is filtered and the residues are resubjected to the above treatment with fresh methanol. The operation is repeated 3 times. The methanol phases are combined and evaporated under vacuum. The residue is agitated with 200 ml of ethyl ether. The ether-insoluble material is recovered by filtration and dissolved in 3 l of water and the solution is extracted with normal butanol saturated with water (3 l then 2×2 l).

The butanol phases are combined and evaporated under vacuum.

The residue (about 150 g) is dissolved in 1.5 l of water and dialyzed against pure water for 4 days, the water being renewed daily. The contents of the dialysis cell are lyophilized.

An additional purification is advantageously carried out: the lyophilizate is dissolved in 300 ml of methanol and discharged into 1.5 l of ether. The precipitate, consisting of the mixture of saponins, is recovered by filtration and dried overnight under vacuum in the presence of $P_2O_5$. The average yield is 30 g.

Example 3

Preparation of mixtures of saponins from lucerne roots at a controlled pH

The procedure is as described in Example 2.

Amberlite IRN 77 cation exchange resin (50 g) is then suspended in 100 ml of water and the mixture is placed in a glass column closed at its lower part by a cock.

The resin is regenerated with 90 ml of three-fold-diluted hydrochloric acid until the eluent has an acid pH.

The resin is then rinsed to neutral pH with 500 ml of distilled water.

5.27 g of the mixture of saponins obtained in Example 2 are dissolved in a mixture of 30 ml of water and 10 ml of ethanol and the solution is then passed over the column of resin. The eluate (200 ml) produced by eluting the column with water is separated into two. One half is frozen and then lyophilized to give 2.29 g of saponins in the acid form, which are collected.

The other half is rendered alkaline to pH 10 with a base, in particular $NH_4OH$. This part is lyophilized to give 2.44 g of saponin salt, in particular the ammonium salt.

Example 4

Preparation of a mixture of saponins from roots of Medicago romanica

The procedure is as described in Example 2 except that roots of Medicago romanica are used.

This gives a powdered dry extract of saponins from roots of Medicago romanica.

Example 5

Preparation of a mixture of saponins from stems of Medicago arborea

The procedure is as described in Example 2 except that finely ground stems of Medicago arborea are used.

Example 6

Preparation of a mixture of sapogenins from Medicago sativa

The powdered product obtained at the end of Example 2, consisting of a mixture of saponins from roots of Medicago sativa, is dissolved in 250 ml of 6.5% aqueous $HClO_4$. The solution is divided up into 3 glass tubes, which are sealed. These tubes are heated at 140° C. for 2 h in an oven. After cooling, the tubes are opened and the precipitate formed is collected by filtration on a no. 3 glass frit. The precipitate is washed to neutral pH with distilled water and dried under vacuum over $P_2O_5$ in a desiccator for 24 h.

The corresponding dry precipitate weighs about 1.1 g and contains the desired mixture of sapogenins.

Example 7

Preparation of liposomes containing sapogenins from Medicago sativa in their bilayer 0.01 g of the mixture of sapogenins obtained in Example 6 is solubilized in 10 ml of methanol and 60 ml of dichloromethane. 5 g of a mixture of soya lecithin and β-sitosterol in a weight ratio of 9/1 are added and the resulting mixture is agitated until solubilization has taken place. It is heated at 60° C. for 1 hour in a rotary evaporator flask.

The lipid film deposited on the inner wall of the flask is then taken up with 44.99 g of distilled water and the mixture is agitated for 3 h at room temperature.

Sonication is then carried out for 10 min at a power of 150 W at 4° C.

The average size of the liposomes obtained is 125.2±2.3 nm.

Preferably, this suspension of liposomes is gelled by being mixed with 50 g of a 1.25% gel of Carbopol 940®, separately prepared in conventional manner. This gives about 100 g of a gelled suspension of liposomes partially encapsulating a mixture of sapogenins from roots of Medicago sativa, the sapogenin concentration of which is about 0.01%, based on the total weight of the gelled suspension.

It can be seen that compositions having a variable proportion of lucerne extract can be obtained as a function of the dilution carried out, which constitutes a particularly easy mode of formulation.

Example 8

Preparation of a gelled suspension of liposomes containing a mixture of saponins from lucerne roots A powdered lipid mixture containing 90% of soya lecithin and 10% of beta-sitosterol is prepared by the method described in the document EP-B1-0 087 993=U.S. Pat. No. 4,508,703, employing the atomization technique.

4 g of this lipid mixture are dispersed, with magnetic stirring, in 96 g of an aqueous solution prepared by dissolving 2 g of the mixture of saponins according to Example 2 in 94 g of water. Stirring is maintained for 2 h at room temperature, after which the mixture is homogenized by ultrasound at 4° C. for 10 min at a power of 150 W.

The average size of the liposomes obtained is about 73 nm.

Preferably, this suspension of liposomes is gelled by being mixed with 100 g of a 1.25% gel of Carbopol 940®, separately prepared in conventional manner. This gives about 200 g of a gelled suspension of liposomes partially encapsulating a mixture of saponins from lucerne roots, the saponin concentration of which is about 1%, based on the total weight of the suspension.

It can be seen that compositions having variable proportions of lucerne extracts can be obtained as a function of the dilution carried out, which constitutes a particularly easy mode of formulation.

Example 9

Test for activity of saponins from roots of Medicago sativa on renewal of the epidermis A. In Petri dishes of diameter 35 mm, 50,000 transformed human keratinocytes are inoculated into 2 ml of EMEM-C (EMEM-C: EMEM complemented with non-essential amino acids) to which 1% by volume of FCS (FCS=fetal calf serum) has been added.

Incubation is carried out for 24 h at a temperature of 37° C.

After this 24 h incubation period, the media are renewed with a medium which is identical but respectively contains different concentrations of the test products, as defined below. The tests are performed in triplicate and control dishes, containing only the solvent for the product tested, are provided.

Incubation is carried out for 6 days at a temperature of 37° C. under an atmosphere of air containing 5% of $CO_2$.

After the 6-day incubation period, the cells are detached with trypsin and counted with the apparatus known as a Coulter Counter.

The products tested have the following compositions:

Product $I_1$ of the invention

This is a purified mixture of saponins from lucerne roots, such as obtained in Example 2, solubilized in EMEM-C.

Product $I_2$ of the invention

This is a mixture of saponins from lucerne leaves, such as obtained by a method identical to that of Example 2, solubilized in DMSO.

Product $I_3$

This is an aqueous extract of the aerial parts of lucerne, commercially available under the name "aqueous extract of lucerne" from Sochibo, also solubilized in the culture medium EMEM-C.

These products are introduced into the culture medium at non-cytotoxic concentrations: 25 μg (dry extract) per ml of culture medium and 100 μg/ml of culture medium.

The results obtained are listed in Table I, which indicates the following: for the control dishes and the dishes treated with the products $I_1$, $I_2$ and $I_3$, the average number of cells per dish after the six-day incubation period, and for the treated dishes, the activity A of the products tested, calculated from the number of cells in each category of dish:

$$A = \frac{\text{treated dish} - \text{control dish}}{\text{control dish}} \times 100$$

A statistical study showed that the differences between the number of cells in the treated dishes and the control dishes, after incubation, were all significant.

Table I shows that, at lower concentration, the product $I_2$ (saponins from leaves) according to the invention is more active than the commercial extract $I_3$, whereas at higher concentration, the product $I_1$ (saponins from roots) according to the invention is the most active.

Thus it is clearly apparent that the lucerne saponins according to the invention are more effective at multiplying the cells of the epidermis than a non-specific extract of the aerial parts of lucerne.

B. A test for activity on the multiplication of human keratinocytes was also performed with two other products, $I_4$ and $I_5$. The operating conditions are the same as those stated above except that only 0.5% of FCS is added to the culture medium EMEM-C.

Product $I_4$ of the invention

This is the fraction in the acid form of the mixture of saponins from lucerne roots, prepared in Example 3, solubilized in DMSO.

Product $I_5$ of the invention

This is the fraction in the form of the ammonium salt of the mixture of saponins from lucerne roots, prepared in Example 3, solubilized in EMEM-C.

The products $I_4$ and $I_5$ are tested at a non-cytotoxic concentration of 25 μg (dry extract) per ml of culture medium.

The results obtained are listed in Table II, which indicates the average number of cells per dish, after six days of incubation, and the activity of the products $I_4$ and $I_5$ compared with the control dishes.

TABLE II

| DMSO control | EMEMC control | $I_4$ acid fraction | | $I_5$ salt fraction | |
|---|---|---|---|---|---|
| No. ¢/dish* | No. ¢/dish* | No. ¢/dish* | A % | No. ¢/dish* | A % |
| 112,140 ± 1,395 | 137,326 ± 4,212 | 172,973 ± 10,957 | 54% (S) | 160,140 ± 617 | 17% (S) |

(*) = cells per dish
(S) = statistically significant

The results in Table II clearly show that both the fractions are active on the multiplication of the keratinocytes of the human epidermis. However, the fraction in the acid form of the mixture of saponins from lucerne roots seems to be much more active than the fraction in the salified form.

TABLE I

| Product Concentration | Control Culture medium | Control DMSO | Lucerne roots ($I_1$) | | Lucerne leaves ($I_2$) | | Commercial extract ($I_3$) | |
|---|---|---|---|---|---|---|---|---|
| μg/ml | No. ¢/dish | No. ¢/dish | No. ¢/dish* | A % | No. ¢/dish* | A % | No. ¢/dish* | A % |
| 0 | 145,280 ± 6,390 | 152,813 ± 5,794 | | | | | | |
| 25 | | | 173,747 ± 1,794 | +19.6 | 204,333 ± 19,656 | +34 | 171,760 ± 2,214 | +18 |
| 100 | | | 214,153 ± 568 | +47 | 1,755,497 ± 9,643 | +15 | 178,580 ± 3,304 | +23 |

*Number of cells per dish

Example 10

Test for activity of saponins from roots of Medicago romanica on renewal of the epidermis The procedure is as described in Example 9 except that the product of the invention used is a mixture of saponins from roots of Medicago romanica, such as obtained in Example 4, solubilized in DMSO.

The results obtained are in Table III below:

TABLE III

| Product tested | No. ¢/dish* × $10^{-3}$ | Activity | Significance $p < 0.05$ |
|---|---|---|---|
| DMSO control | 153 ± 4 | | |
| +10 µg/ml | 164 ± 3 | +7% | S |
| +25 µg/ml | 172 ± 5 | +12% | S |
| +50 µg/ml of product of the invention (Ex. 4) | 213 ± 9 | +39% | S |

The results of the tests reported in Table III clearly show that the product of the invention, namely a mixture of saponins from roots of Medicago romanica, has a significant activity on the multiplication of the keratinocytes of the human epidermis.

Example 11

Test for activity of saponins from stems of Medicago arborea on renewal of the epidermis The procedure is as described in Example 9 except that a mixture of saponins from stems of Medicago arborea, obtained in Example 5, solubilized in DMSO, is used.

The results obtained are listed in Table IV.

TABLE IV

| Product tested | No. ¢/dish* × $10^{-3}$(sic) | Activity | Significance $P < 0.05$ |
|---|---|---|---|
| DMSO control | 153 ± 4 | | |
| +10 µg/ml | 154 ± 5 | +1% | NS |
| +25 µg/ml | 227 ± 7 | +48% | S |
| +50 µg/ml of product of the invention (Ex. 5) | 235 ± 5 | +53% | S |

The test results reported in Table IV clearly show that the saponins from stems of Medicago arborea have a significant activity on the multiplication of the keratinocytes of the human epidermis.

Example 12

Demonstration of the activity of saponins from roots of lucerne (Medicago sativa) on the synthesis of Collagen by human fibroblasts Fibroblasts are taken from the skin of a 55-year-old white woman during a face lift and the skin is cut into thin strips, which are placed in a 0.25% solution of trypsin overnight at 4° C. The epidermal cells then separate from the dermis after scraping.

The strips of dermis obtained in this way are cut into cubic fragments with a side length of about 1 mm, which are called explants. These explants are deposited on a film of GIBCO E 199 medium supplemented with 2 mmol/l of L-glutamine and 10% of fetal calf serum, at a rate of 20 explants per culture dish of diameter 100 mm.

The dishes are incubated at 37° C. in a moist atmosphere enriched with $CO_2$ (5%). The medium is renewed twice a week.

When the cells reach confluence around the explants, the fibroblasts are extracted without removing the explants, using a 0.1% trypsin/0.02% EDTA mixture, and the fibroblasts are reimplanted in a renewed culture medium. Some of the dishes serve as controls and receive renewed medium without the product of the invention, and the other dishes are divided into two batches receiving the product of the invention at either 100 µg/ml or 250 µg/ml respectively, this product of the invention consisting of the mixture of saponins from roots of Medicago sativa, obtained in Example 2.

Incubation is carried out for 24 h in the absence or presence of the product of the invention at the indicated concentration.

After incubation for 24 h, the collagen I secreted by the fibroblasts into the supernatant is assayed by a method similar to that described by RENNARD S. I. et al. in Anal. Biochem. (1980), 104, 205–214.

The results obtained by this assay method are listed in Table V below.

TABLE V

| | Results | | |
|---|---|---|---|
| | Collagen I secreted by fibroblasts (ng/10,000 cells/24 h) | % stimulation | Significance $P < 0.05$ |
| Control culture without product Product of the invention (Ex. 2) | 269 ± 28.9 | 0 | |
| 100 µg/ml | 306.9 ± 34.6 | 14.1% | S |
| 250 µg/ml | 317.2 ± 25.8 | 17.9% | S |

In Table V, the amounts of collagen I secreted by the fibroblasts have been expressed in ng/10,000 cells/24 h.

It will be seen from Table V that the mixture of saponins from roots of Medicago sativa produces a significant activity in stimulating the synthesis of collagen I by the fibroblasts.

In this respect, Shuster et al., in Br. J. Dermatol. (1975), 93, 639–643, entitled "The Influence of age and sex on skin thickness, skin collagen and density", have demonstrated a decrease in the collagen content of the skin between 15 and 93 years of age. Furthermore, collagen forms the basis of the architecture of the dermis, which is why there is interest in a product capable of exerting a stimulating effect on collagen synthesis.

Example 13

Demonstration of the activity of the lucerne saponins according to the invention on the hair system The test is based on a study of the activity of the products according to the invention on the hair cycle of Sprague Dawley rats, all 23 days old. At this age, the hair cycles of all the animals are still synchronous. The rats are shaved on the lower part of the back on day 24.

The test products are subsequently applied (from day 25) up to day 65, on 6 days out of 7, at a dose which changes with the weight of the animals. This dose is 0.5 ml on day 25 and reaches 2 ml on day 65.

At approximately regular time intervals (about every 3 days), tweezers are used to remove a tuft of hairs from the animal's left side. 10 hairs selected at random from this tuft are observed and the number of hairs in the anagenetic phase are counted. The percentage of hairs in the anagenetic phase (growth phase) is thus determined as a function of time for each group of 10 animals.

The study is performed on 30 rats divided into 3 groups of 10 animals. The first group receives a preparation containing 0.1% of the product of Example 2 (mixture of saponins from lucerne roots) in an excipient. Composition of the excipient per 100 g: water 15 g, propylene glycol 20 g, 95% alcohol 65 g. The second group receives only the above-mentioned excipient. The third group is the control group and does not receive any product.

Figure 1:
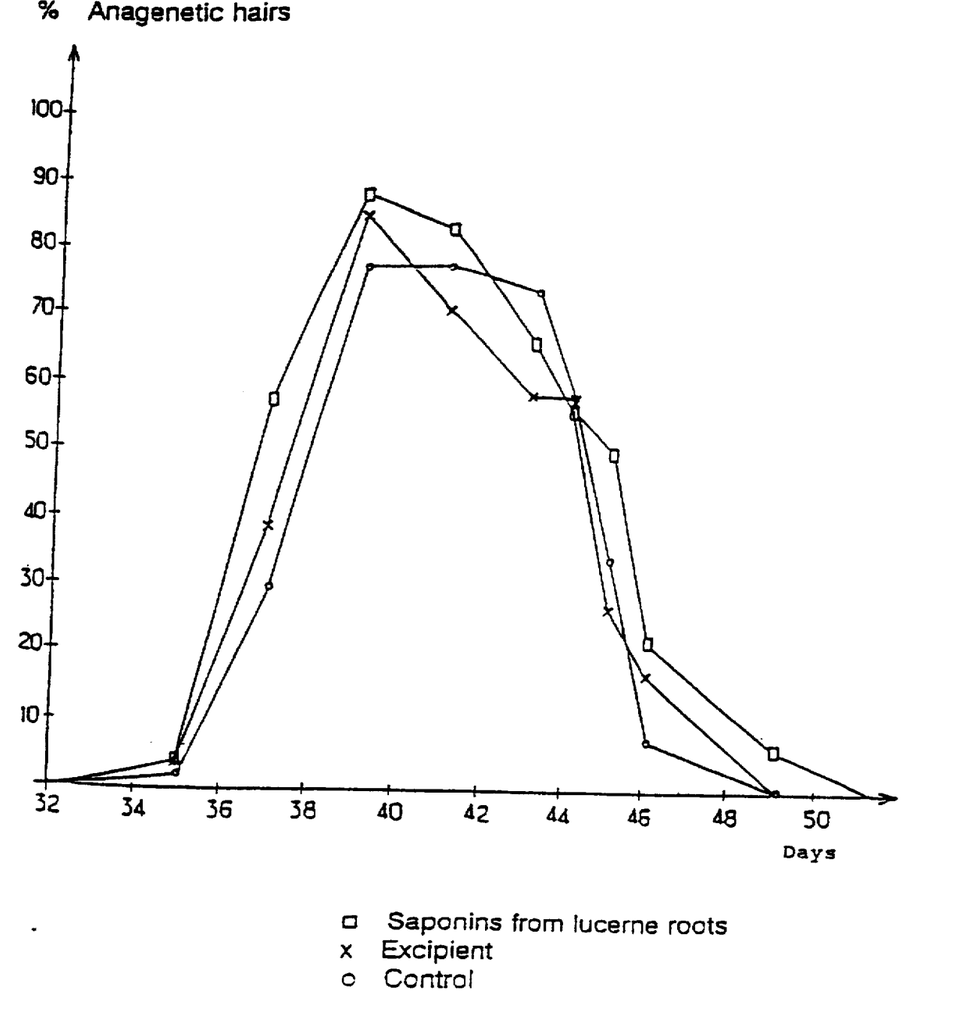

The results of this trichokinetic study (trichogram as a function of time) are collated as average values in Table VI and represented in the attached single FIGURE.

TABLE VI

| | Percentage of anagenetic hairs | | | | | | | |
|---|---|---|---|---|---|---|---|---|
| | 37 days | 39 d | 41 d | 43 d | 44 d | 45 d | 46 d | 49 d |
| Composition saponins + excipient (invention) | 59 | 89 | 83 | 66 | 56 | 50 | 22 | 6 |
| Excipient only | 39 | 86 | 71 | 58 | 59 | 27 | 17 | 0 |
| Control | 30 | 78 | 78 | 74 | 57 | 31 | 7 | 0 |

This FIGURE shows the percentage of hairs in the anagenic phase on the ordinate and the number of days on the abscissa.

The curve joining the squares corresponds to the results obtained with the mixture of saponins from lucerne roots of Example 2 according to the invention, the curve joining the crosses is obtained with the excipient and, finally, the curve joining the dots is obtained with the control group which does not receive any product.

It is seen that the number of hairs in the anagenetic phase increases much more rapidly in the group receiving the mixture of saponins from lucerne roots according to the invention than in the group receiving the excipient or in the control group. It is also seen that the anagenetic phase extends over a longer period.

Thus it is clear that, by extending the duration of the anagenetic phase, the lucerne extracts according to the invention delay hair loss very appreciably and promote regrowth.

Various Examples of the formulation of cosmetic or pharmaceutical compositions, promoting hair regrowth and/ or delaying hair loss and/or promoting renewal or growth of the epidermis, are now given below.

Example 14

Gel for regulating the epidermis 0.2 g of saponins from roots of Medicago romanica, such as obtained in Example 4, is dissolved in 49.2 g of distilled water and this solution is then gelled by adding 50 g of a neutralized 3% gel of Carbopol 940®.

This gel can be applied twice a day over a 4-month course of treatment.

Example 15

Eye contour gel

The following composition is prepared:

| Component A | |
|---|---|
| saponin from Medicago sativa, such as obtained in Example 2 | 0.20 |
| polyoxyethyleneated vitamin E succinate | 0.10 |
| 10α-disabolol (sic) | 0.1 |
| hyaluronic acid | 0.20 |
| propylene glycol | 4.00 |
| water | 83.4 |
| Component B | 12.00 |
| 2.5% gel of Carbopol 980 | |

All the components A are first mixed in the water, and component B is introduced to give a gel, which can be used twice a day for its activity in combating loosening of the eye contour skin.

Example 16

Treating mascara for promoting eyelash growth

The following composition is prepared:

| mixture of saponins from Medicago sativa, such as obtained in Example 2 | 0.2 |
|---|---|
| glycerol monostearate | 10 |
| stearic acid | 10 |
| triethanolamine | 5 |
| isopropyl myristate | 15 |
| beeswax | 25 |
| distilled water | 27.8 |
| gelatin | 2 |
| black iron oxide | 5 |

This composition, forming a mascara, is used in conventional manner on the eyelashes and has the advantage of promoting eyelash growth.

Example 17

Liposomal anti-ageing gel

The gel used is such as prepared according to Example 7 except that the distilled water is replaced with an aqueous solution containing 0.2% by weight of hydroxyproline.

This gel is applied to the skin, firming it and reducing the wrinkles.

Example 18

Lotion for combating the loss of hair, in particular on the scalp

The following composition is prepared:

| mixture of saponins from lucerne roots, in the acid form (Example 3) | 0.1 g |
|---|---|
| panthenol | 0.1 g |
| keratin hydrolyzate | 0.3 g |
| fragrance | 0.1 g |
| 20% alcohol qsp | 100 g |

Example 19

Styling gel for combating the loss of hair

The following composition is prepared:

| | |
|---|---|
| extract of aerial parts of lucerne, according to Example 1 | 0.3 g |
| neutralized 1.50% gel of Carbopol 940 ® | 45 g |
| Phytantriol ® | 0.1 g |
| protein-zinc complex | 0.1 g |
| preservative | 0.05 g |
| water qsp | 100 g |

The mixture of saponins is first dissolved in the water, after which the Phytantriol, the protein-zinc complex, the preservative and finally the Carbopol940® are added.

The gel obtained is applied to the areas of hair follicle loss for 6 months, morning and evening.

Example 20

Treating gel for combating seborrheic alopecia

The following composition is prepared:

| | |
|---|---|
| mixture of saponins from lucerne roots of Example 2 | 0.2 g |
| fragrance | 0.1 g |
| protein-zinc complex | 0.05 g |
| 1.50% gel of Carbopol 940 ® | 45 g |
| water qsp | 100 g |

The gel is prepared by the procedure described in Example 9.

This gel can be applied to the hair for 6 months, morning and evening.

Example 21

Treating cream for combating cutaneous senescence

A cream containing 0.2% of extract of lucerne roots is prepared in the following manner:

| | |
|---|---|
| Composition A (percentage by weight) | |
| Tefosse 1500 ® from Gattefosse | 7.00 |
| cetyl alcohol | 2.00 |
| Primol 352 ® from ESSO | 25.00 |
| Composition B (percentage by weight) | |
| demineralized water | 54.40 |
| Carbopol 940 ® from Polyplastic | 0.30 |
| triethanolamine | 0.30 |
| Composition C (percentage by weight) | 0.80 |
| Germaben II ® from Seppic | |
| Composition D (percentage by weight) | |
| demineralized water | 10.00 |
| mixture of saponins from lucerne roots of Example 2 | 0.20 |

Composition A is heated to 75° C. and the Carbopol 940® is then dispersed in the water of composition B. The gel is neutralized with triethanolamine. Solution B is heated to 75° C. Composition A is emulsified in composition B at 75° C. The emulsion is cooled to 40° C., with agitation.

Composition C is then added. The components of composition D are premixed and composition D is then added to the formulation. The resulting mixture is homogenized and cooled to room temperature to give a cream.

This cream can be applied twice a day over a 6-month course of treatment to give progressive disappearing of senescence spots.

We claim:

1. A method for promoting hair growth, combating seborrheic alopecia, and delaying hair loss, comprising the topical application on the desired area to be treated comprising hair, and scalp, an amount effective for achieving said topical treatment of an active ingredient consisting essentially of at least one Medicago component selected from the group consisting of Medicago triterpene saponins, the corresponding sapogenins, Medicago plant extracts containing at least one of said triterpene saponins, and Medicago plant extracts containing at least one of said sapogenins.

2. The method of claim 1, wherein said method is for promoting eye lash growth.

3. The method according to claim 1 wherein the Medicago component is at least partially incorporated into a hydrated lipidic lamellar phase or into liposomal vesicles.

4. The method according to claim 1 wherein the Medicago component is obtained by extraction from a Medicago plant part selected from the group consisting of aerial parts and roots.

5. The method according to claim 1 wherein the sapogenin and Medicago plant extract are obtained from calluses obtained by the in vitro culture of tissue of Medicago.

6. The method according to claim 1 wherein the saponin is a saponin containing a carboxyl group.

7. The method according to claim 1 wherein the Medicago plant extract is obtained from a Medicago plant selected from the group consisting of Medicago satira, Medicago lupulina, Medicago truncatula, Medicago laciniata, Medicago littoralis, Medicago falcata, Medicago media, Medicago minima, Medicago varia, Medicago arborea and Medicago romanica.

8. The method according to claim 1 wherein the Medicago plant extract is obtained from a Medicago plant part in dry form, by contacting said Medicago plant part in dry form with a solvent selected from the group consisting of water, alcohols containing from 1 to 4 carbon atoms, and organic esters containing from 3 to 6 carbon atoms, and a mixed solvent based on a mixture of said solvents.

9. The method according to claim 7 wherein the extraction solvent is selected from the group consisting of methanol, ethanol, a methanol/water mixture, or an ethanol/water mixture.

10. The method according to claim 1 wherein a mixture of saponins is used and wherein the mixture is obtained by precipitation of the plant extract on an apolar solvent.

11. The method according to claim 10 wherein the apolar solvent is miscible with the extraction solvent.

12. The according to claim 10 wherein the mixture of saponins is subjected to a treatment converting to the acid form those saponins which contain a carboxyl group as a salt.

13. The method according to claim 1 wherein the sapogenins are obtained from the saponins by hydrolysis of the glycosidic linkages of the saponins.

14. The method according to claim 13 wherein the hydrolysis is an acid hydrolysis.

15. The method according to claim 14 wherein the abovementioned sapogenin is selected from the group consisting of lucernic acid, medicagenic acid, zanhic acid, bayogenin, hederagenin and soyasapogenols A, B, C and E.

16. The method according to claim 3 wherein the abovementioned saponin is introduced into the aqueous phase of the hydrated lipidic lamellar phase or the liposomes at a concentration of between 0.01% and 5% by weight, based on the total weight of said aqueous phase.

17. The method according to claim 3 wherein the sapogenin is incorporated into the lipidic phase of the hydrated lamellar phase or the liposomes at a concentration of between 0.01% and 30% by weight of said lipidic phase.

18. The method according to claim 17 wherein the sapogenin is incorporated at a concentration of between 0.01% and 10% by weight of this lipidic phase.

19. The method according to claim 4, wherein said aerial part is selected from the group consisting of leaves and stems.

20. A method according to claim 5, wherein said calluses are obtained by the in vitro culture of root tissues of a Medicago plant.

21. The method according to claim 8, wherein said Medicago plant extract is obtained from Medicago plant roots.

22. The method according to claim 14, wherein said hydrolysis comprises using as an acid a halogen-containing acid.

23. The method according to claim 22, wherein said halogen-containing acid is selected from the group consisting of perchloric acid, fluoboric acid and trifluoroacetic acid.

* * * * *